US006451063B1

(12) United States Patent
Clarkson et al.

(10) Patent No.: US 6,451,063 B1
(45) Date of Patent: *Sep. 17, 2002

(54) CELLULASE FOR USE IN INDUSTRIAL PROCESSES

(75) Inventors: Kathleen A. Clarkson, San Francisco, CA (US); Barbara Swanson, San Francisco, CA (US); Deborah Winetzky, South San Francisco, CA (US)

(73) Assignee: Genencor International, Inc., Palo Alto, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/719,506

(22) Filed: Sep. 25, 1996

(51) Int. Cl.[7] .................. D06M 16/00; A23K 1/165; D01C 1/00; D21C 3/00
(52) U.S. Cl. .................. 8/102; 8/107; 510/320; 510/321; 510/392; 510/393; 510/530; 426/623; 426/648; 162/72; 162/91; 162/4; 162/5; 162/158; 435/263; 435/267; 435/277
(58) Field of Search .................. 252/8.91; 510/320, 510/321, 392, 393, 530; 426/623, 648; 8/102, 137; 162/72, 91, 4, 5, 158; 435/263, 267, 277

(56) References Cited

U.S. PATENT DOCUMENTS

| 4,832,864 A | * | 5/1989 | Olson ........................... 8/102 |
| 4,923,565 A | * | 5/1990 | Fuentes et al. ............... 162/72 |
| 5,232,851 A | * | 8/1993 | Cox et al. .................... 435/263 |
| 5,364,501 A | * | 11/1994 | Baret et al. .................... 162/5 |
| 5,434,069 A | * | 7/1995 | Tsaur et al. .................. 510/321 |
| 5,476,608 A | * | 12/1995 | Boyer et al. ................. 510/321 |
| 5,677,151 A | * | 10/1997 | Wilson et al. ................. 435/72 |
| 5,798,327 A | * | 8/1998 | Casteleijn et al. ........... 510/303 |
| 5,871,550 A | * | 2/1999 | Goedegebuur et al. ........ 8/137 |
| 5,877,139 A | * | 3/1999 | Casteleijn et al. ........... 510/303 |
| 6,190,899 B1 | * | 2/2001 | Jones et al. .................. 435/209 |

FOREIGN PATENT DOCUMENTS

| CA | 758488 | * | 5/1967 |
| GB | 2261877 | * | 6/1993 |
| WO | WO 98/13465 | * | 4/1998 |
| WO | WO 99/29821 | * | 6/1999 |

OTHER PUBLICATIONS

Wilson, Methods in Enzymology, vol. 160, pp. 314–323. (month unknown), 1988.*
McGinnis et al, Biochemistry, vol. 32, pp. 8151–8156. (month unknown), 1883.*
McGinnis et al, Biochemistry, vol. 32, pp. 8157–8161 (month unknown). 1993.*
Calza et al., "Purification and Characterization of two β–1, 4–Endoglucanases from *Thermomonospora fusca*," *Biochemistry* (1985) 24:7797–7804. (Month unknown).
Collmer et al., "Cloning and Expression of a Thermomonospora YX Endocellulase Gene in *E. Coli*," *Bio/Technology* 594–601, Sep. 1983.
Ghangas et al., "Cloning of the *Thermomonospora fusca* Endoglucanase E2 Gene in *Streptomyces lividans*: Affinity Purifcation and Functional Domains of the Cloned Gene Product," *Applied and Environmental Microbiology* 54/10:2521–2526, Oct. 1988.
Ghangas et al., Expression of a *Thermomonospora fusca* Cellulase Gene in *Streptomyces lividans* and *Bacillus subtilis*, *Applied and Environmental Microbiology* 53/7:1470–1475, Jul. 1987.
Irwin et al., "Activity Studies of Eight Purified Cellulases: Specificity, Synergism, and Binding Domain Effects," *Biotechnology and Bioengineering* 42:1002–1013, Oct. 1993.
Irwin et al., "Characterization and Sequence of a *Thermomonospora fusca* Xylanase," *Applied and Envoromental Microbiology* 60/3:763–770, Mar. 1994.
Jung et al., "DNA Sequences and Expression in *Streptomyces lividans* of an Exoglucanase Gene and an Endoglucanase Gene from *Thermomonospora fusca*," *Applied and Envoromental Microbiology* 59/9:3032–3043, Sep. 1993.
Lao et al., "DNA Sequences of Three β–1, 4–Endoglucanase Genes from *Thermomonospora fusca*," *Journal of Bacteriology* 173/11:3397–3407, Jun. 1991.
Lin et al., "Regulation of β–1, 4–Endoglucanase Synthesis in *Thermomonospora fusca*," *Applied and Environmental Microbiology* 53/6:1352–1357, Jun. 1987.
Maglione et al., "Properties of a Genetically Reconstructed *Prevotella ruminicola* Endoglucanase," *Applied and Environmental Microbiology* 58/11:3593–3597, Nov. 1992.
Spezio et al., "Crystal Structure of the Catalytic Domain of a Thermophilic Endocellulase," *Biochemistry* (1993) 32:9906–9916. (Month unknown).
Wilson, "Biochemistry and Genetics of Actinomycete Cellulases," *Critical Reviews in Biotechnology* (1992) 12(1/2):45–63. (Month unknown).
Wood et al., "Cyclic AMP Levels During Induction and Repression of Cellulase Biosynthesis in *Thermomonospora curvata*," *Journal of Bacteriology* (1984) 160/3:1047–1054. (Month unknown).

* cited by examiner

*Primary Examiner*—Alan Diamond
(74) *Attorney, Agent, or Firm*—Genencor International, Inc

(57) ABSTRACT

A method for treating cellulosic materials is disclosed which comprises contacting the cellulosic material with a cellulase obtainable from *Thermomonospora fusca* corresponding to E5 or a derivative thereof. Particularly preferred methods comprise stonewashing and detergent cleaning of cotton fabrics, the production of paper products, as an additive to animal feed and in the production of food, starch, ethanol and sugar.

11 Claims, 6 Drawing Sheets

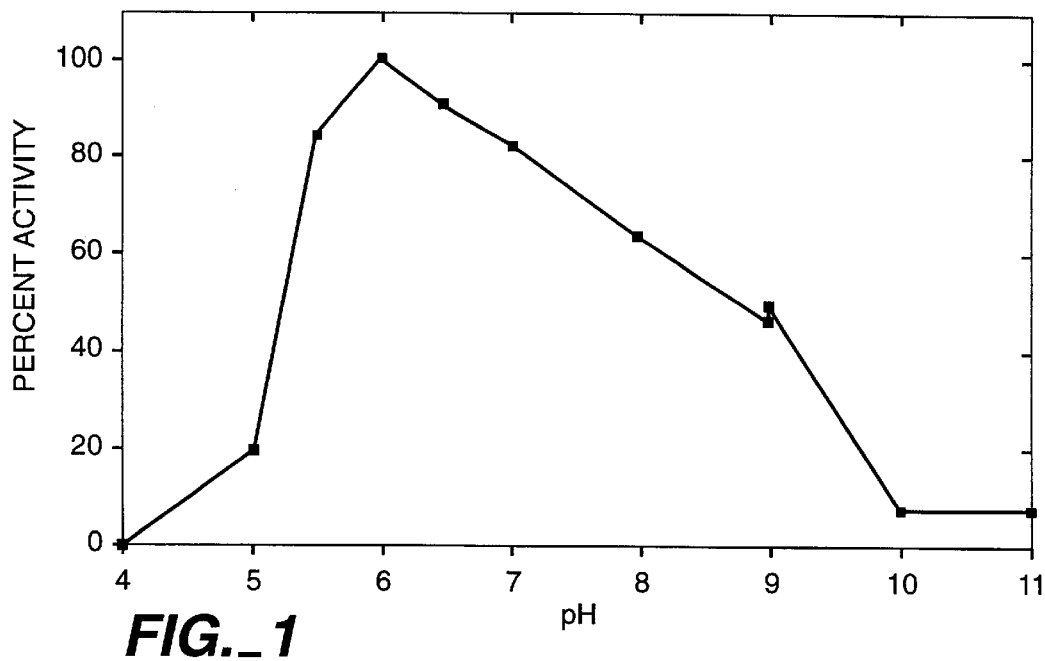
FIG._1
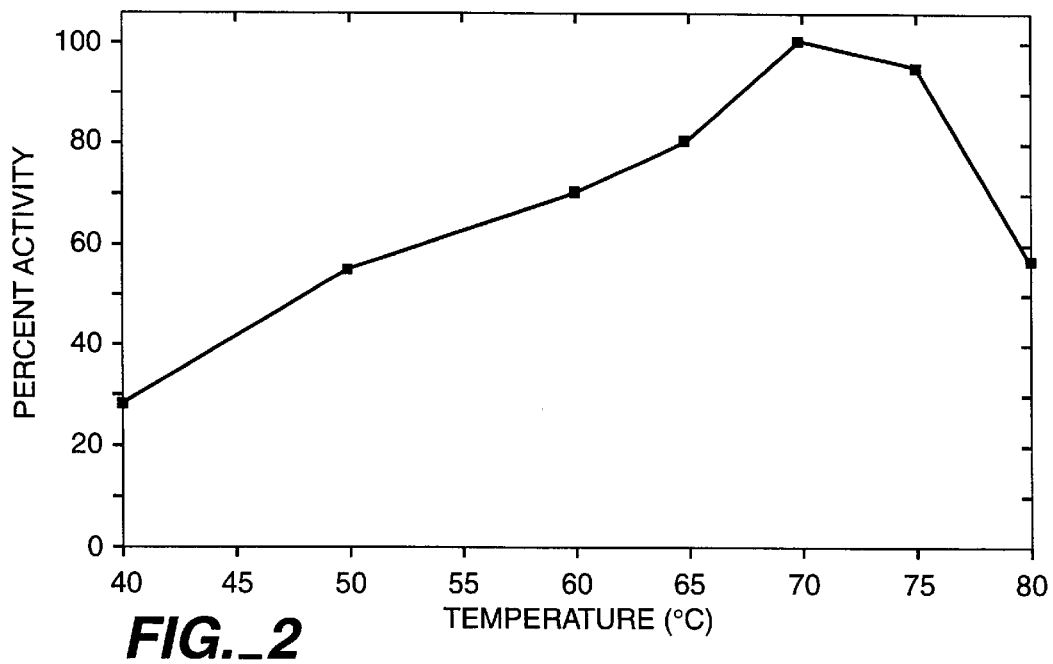
FIG._2

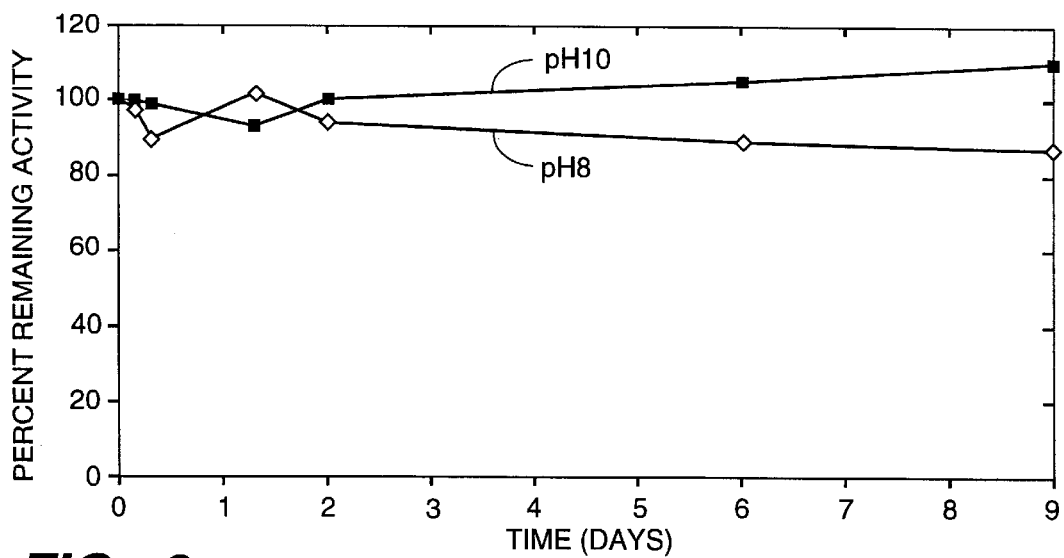
FIG._3
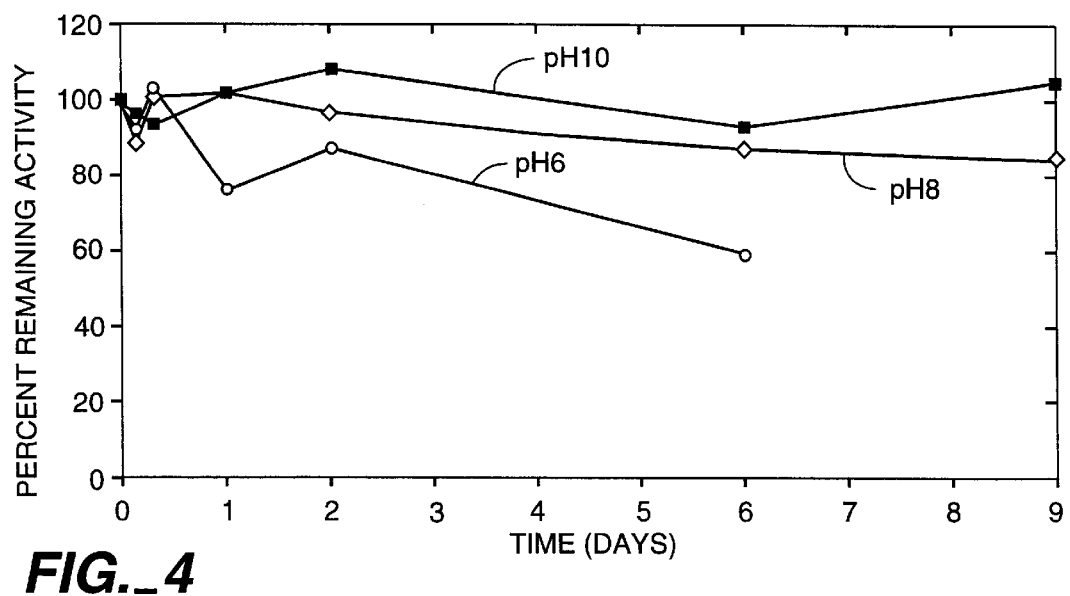
FIG._4

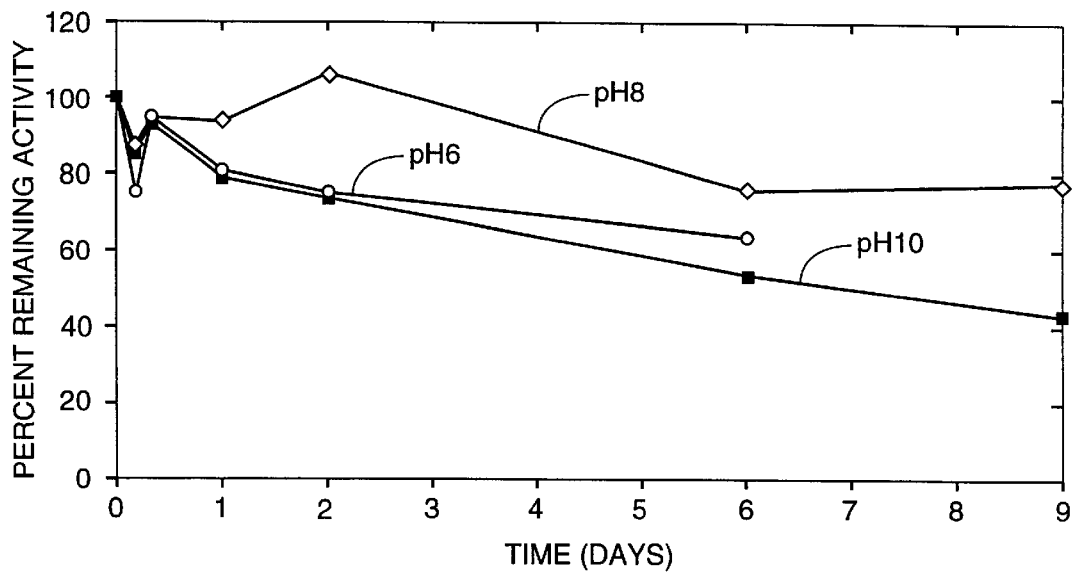
FIG._5
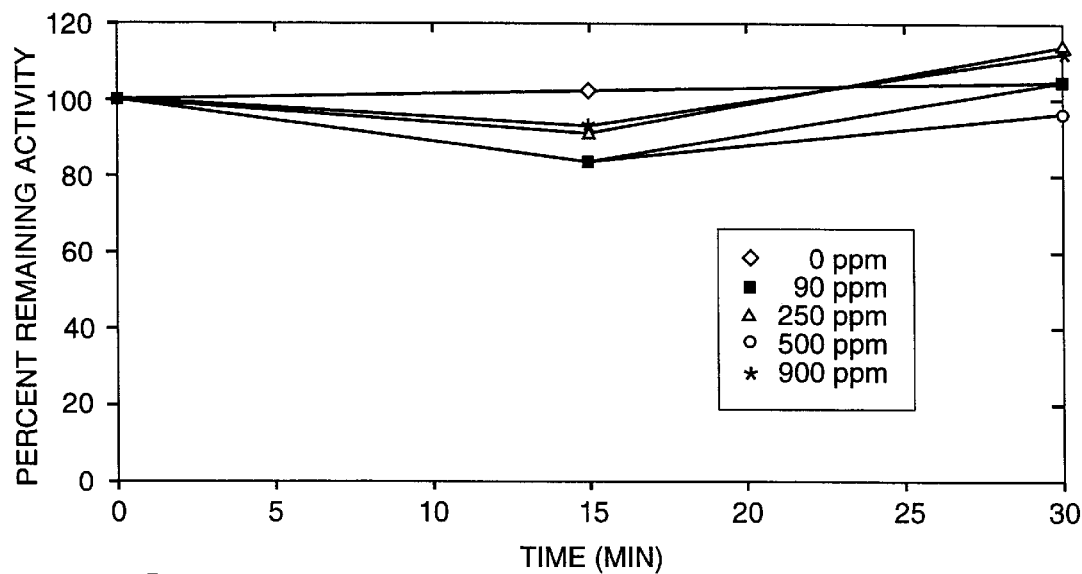
FIG._6

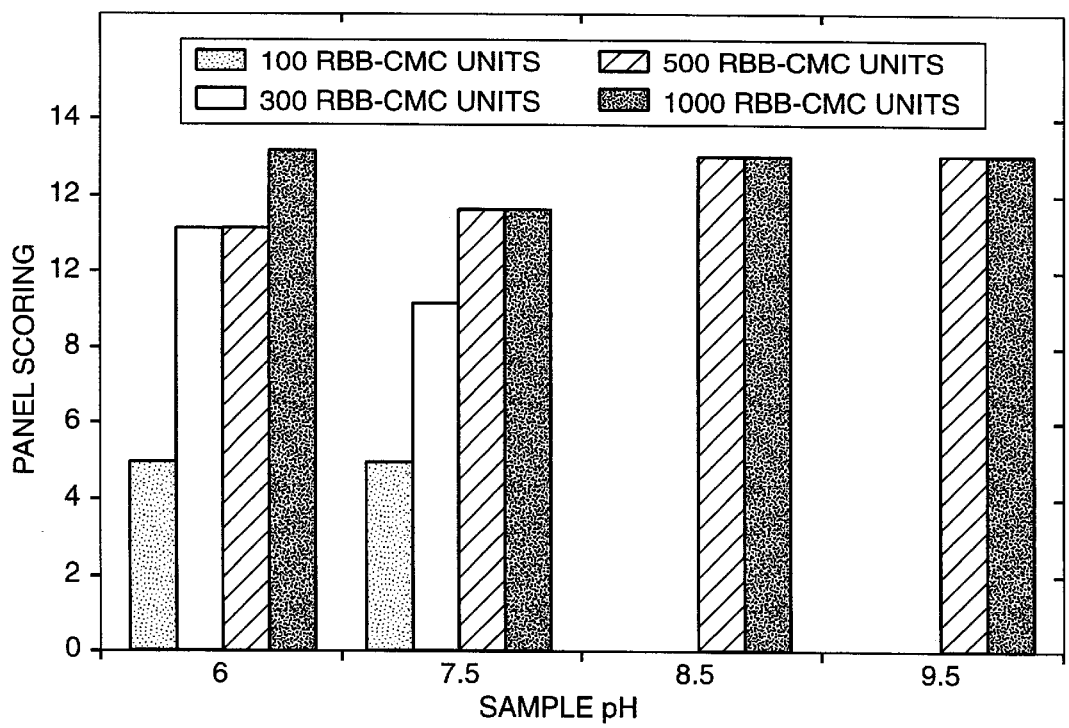
FIG._7
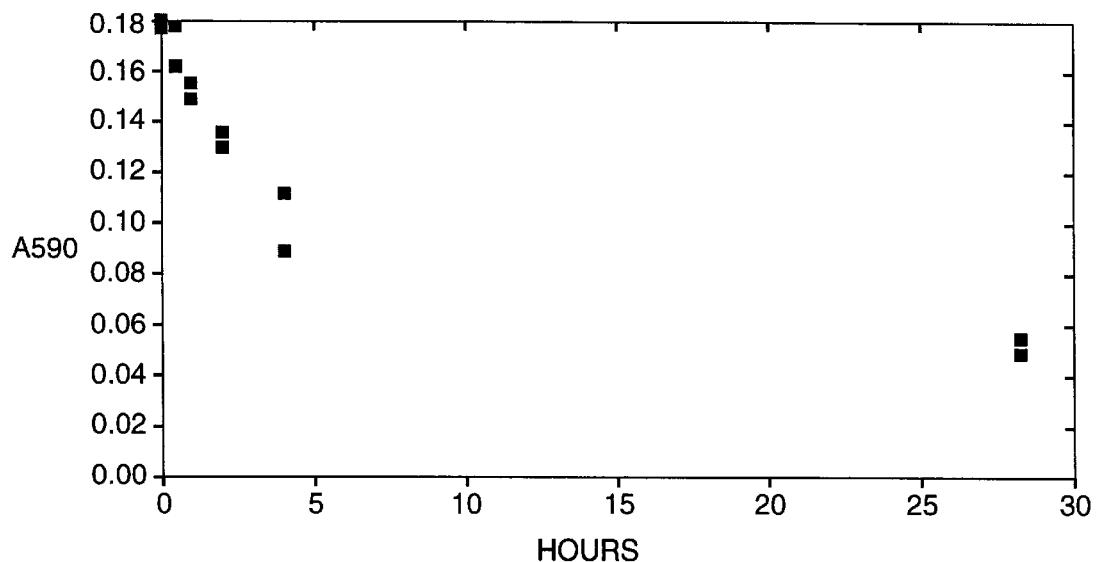
FIG._8

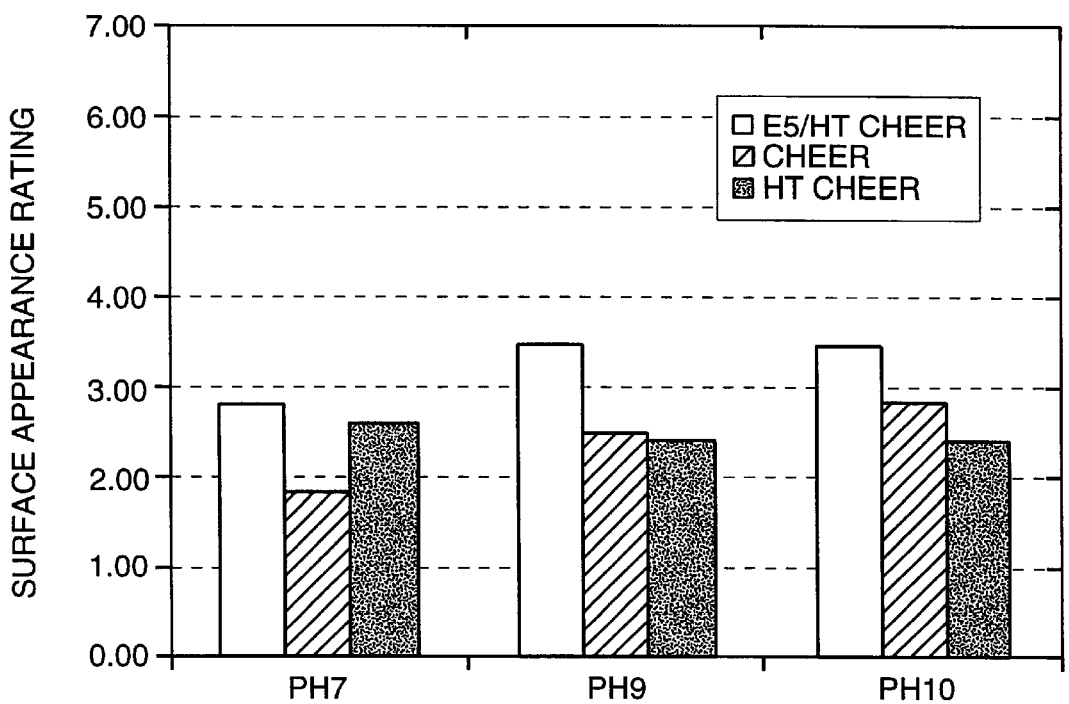
FIG._9
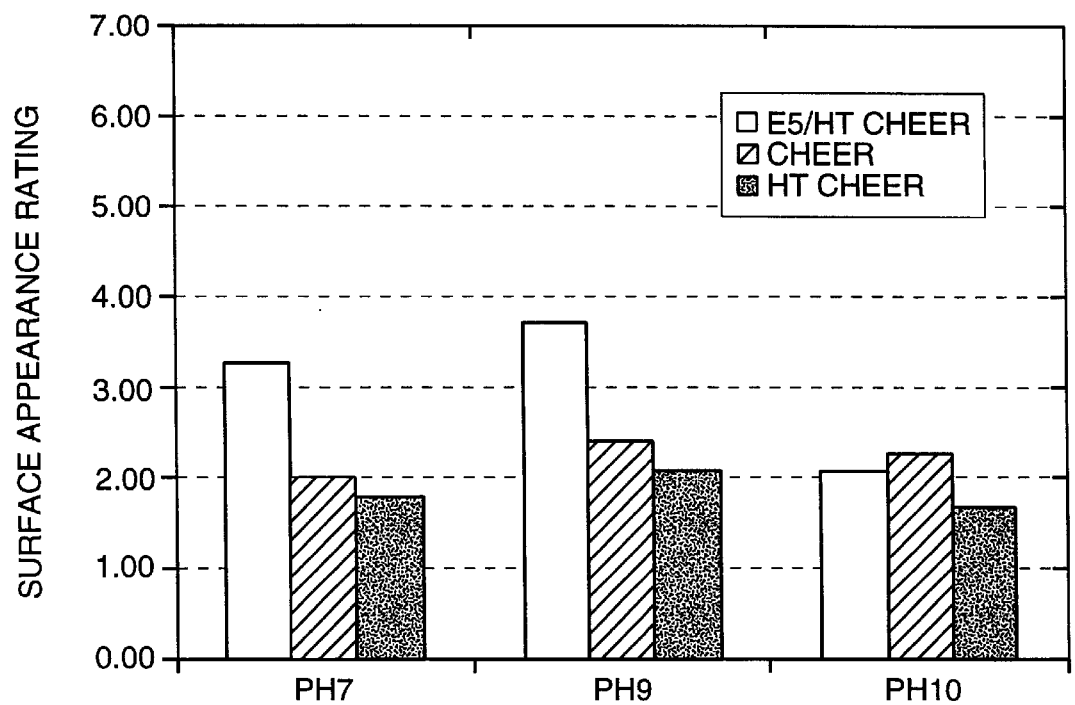
FIG._10

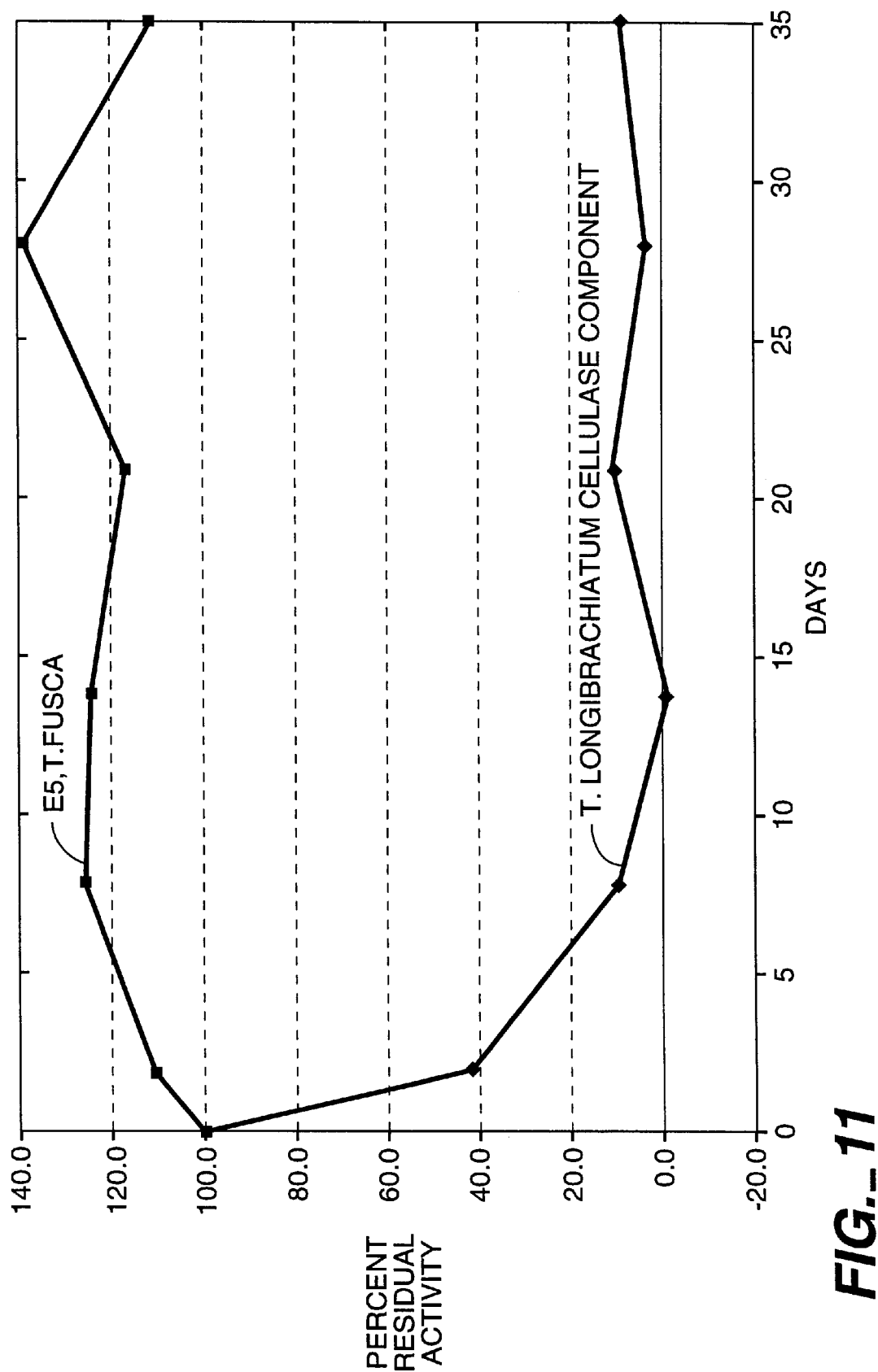
FIG._11

CELLULASE FOR USE IN INDUSTRIAL PROCESSES

BACKGROUND OF THE INVENTION

The present invention is directed to methods comprising the use of cellulases in industrial processes and compositions therefor. In particular, the present invention is related to treating textiles, e.g., laundering and processing, with cellulase derived from *Thermomonospora fusca* which is particularly well suited for that purpose. The present invention is further related to the use of cellulase derived from *Thermomonospora fusca* to enhance the digestibility of animal feed, in detergents, in the treatment of pulp and paper and in the production of starch and treatment of by-products thereof.

Cellulases are enzymes which hydrolyze cellulose (β-1, 4-D-glucan linkages) and produce as primary products glucose, cellobiose and cellooligosaccharides. Cellulases are produced by a number of microorganisms and comprise several different enzyme classifications including those identified as exo-cellobiohydrolases (CBH), endoglucanases (EG) and β-glucosidases (BG) (M. Schulein, Methods in Enzymology, vol. 160, pp. 235–242 (1988)). Current theory holds that the enzymes within these classifications can be separated into individual components. For example, microbial cellulase compositions may consist of one or more CBH components, one or more EG components and possibly β-glucosidase. The complete cellulase system comprising CBH, EG and BG components synergistically act to convert crystalline cellulose to glucose. The exo-cellobiohydrolases and the endoglucanases act together to hydrolyze cellulose to small cello-oligosaccharides. The oligosaccharides (mainly cellobioses) are subsequently hydrolyzed to glucose by a major β-glucosidase.

Cellulases and components thereof, used either singularly or in combination, are known to be useful in detergent compositions and for treating textiles. In the textile industry, during or shortly after the manufacture of cotton-containing fabrics, it is known to treat such fabrics with cellulase to impart desirable properties to the fabric. One purpose of this treatment is to remove fuzz, i.e., untangled fiber ends that protrude from the surface of a yarn or fabric, and pills, i.e., bunches or balls of tangled fibers that are held to the surface of a fabric by one or more fibers. Accordingly, in the textile industry, cellulase has been used to improve the feel and/or appearance of cotton-containing fabrics, to remove surface fibers from cotton-containing knits, and also for imparting a stone washed appearance to cotton-containing denims. In particular, Japanese Patent Application Nos. 58-36217 and 58-54032 as well as Ohishi et al., "Reformation of Cotton Fabric by Cellulase" and "What's New—Weight Loss Treatment to Soften the Touch of Cotton Fabric" Japan Textile News, (December 1988) each disclose that treatment of cotton-containing fabrics with cellulase results in an improved feel for the fabric. It is generally believed that this cellulase treatment removes cotton fuzzing and/or surface fibers which reduces the weight of the fabric. The combination of these effects imparts improved feel to the fabric.

Clothing made from cellulose fabric, such as cotton denim, is stiff in texture due to the presence of sizing compositions used to ease manufacturing, handling and assembling of clothing items and typically has a fresh dark dyed appearance. One desirable characteristic of indigo-dyed denim cloth is the alteration of dyed threads with white threads, which gives denim a white on blue appearance. For example, after a period of extended wear and laundering, the clothing items, particularly denim, can develop in the panels and seams localized areas of variation in the form of a lightening in the depth or density of color. In addition, a general fading of the clothes, some pucker in seams and some wrinkling in the fabric panels can often appear. In recent years such a distressed or "stonewashed" look, particularly in denim clothing, has become very desirable to a substantial proportion of the public.

Previous methods for producing the distressed look included stonewashing of a clothing item or items in a large tub with pumice stones having a particle size of about 1 to 10 inches and with smaller pumice particles generated by the abrasive nature of the process. Typically the clothing item is tumbled with the pumice while wet for a sufficient period such that the pumice abrades the fabric to produce in the fabric panels localized abraded areas of lighter color and similar lightened areas in the seams. Additionally, the pumice softens the fabric and produces a fuzzy surface similar to that produced by the extended wear and laundering of the fabric.

The use of the pumice stones has several disadvantages, including overload damage to the machine motors, mechanical damage to transport mechanisms and washing drums, environmental waste problems from the grit produced and high labor costs associated with the manual removal of the stones from the pockets of the garments. In view of the problems associated with pumice stones in stonewashing, cellulase solutions are used as a replacement for the pumice stones under agitating and cascading conditions, i.e., in a rotary drum washing machine, to impart a "stonewashed" appearance to the denim (U.S. Pat. No. 4,832,864).

A cellulase system derived from the thermophilic, filamentous, soil bacterium *Thermomonospora fusca* has been detected and the biochemical characteristics of that system and components thereof studied (Wilson, Critical Reviews in Biotechnology, Vol. 12½, pp. 45–63 (1992)). One specific endoglucanase component of the *T. fusca* system, E5, has been sequenced (Lao et al., J. Bacter., vol. 173, pp. 3397–3407 (1991)), and its disulfide arrangement and functional domains described (McGinnis et al., Biochemistry, vol. 32, pp. 8157–8161 (1993)). McGinnis discloses that E5 treated with protease from *Streptomyces lividans* results in a 14 kD cellulose binding domain and a catalytically active 32 kD fragment which had lost the ability to bind to cellulose. Pure catalytically active *S. lividans* protease treated E5 was shown to have similar activity to intact enzyme on CMC. However, mixtures of catalytically active E5 fragments, when combined with intact E3 from *T. fusca* or intact E3 and CBHI from *Trichoderma reesei*, showed decreased performance to similar mixtures containing intact E5 instead of the fragment (PCT Publication No. 96/00281).

Despite intensive research related to the use of cellulases in industrial processes, cellulases known and used in the art have shown significant drawbacks. For example, many cellulases have been problematic due to low activity, poor alkaline or acid stability, poor temperature stability and poor oxidative stability. Surprisingly, Applicants herein have discovered that the E5 cellulase possesses a complement of characteristics which makes its use particularly desirable in certain industrial applications.

SUMMARY OF THE INVENTION

According to the present invention, a method of treating cellulosic material is provided comprising contacting the cellulosic material with a cellulase obtainable from *Ther-*

*momonospora fusca* corresponding to E5, a truncated E5, or a derivative thereof. In a process embodiment of the invention, the cellulosic material comprises cellulose containing fabric and the result of the method is to produce a stonewashed effect or an improvement in the feel and/or appearance of the fabric. In an alternative process embodiment of the invention, the cellulose containing fabric is contacted with an aqueous solution containing a detergent composition comprising a cellulase obtainable from *T. fusca* corresponding to E5, a truncated E5, or a derivative thereof. In yet another process embodiment of the invention, the cellulosic material comprises wood pulp and the addition of cellulase facilitates the production of paper products therefrom. In yet another process embodiment of the invention, the cellulosic material comprises animal feed and the method results in an increase in the digestibility or value of said animal feed. In still further embodiments of the invention, the cellulosic material comprises grain or grain byproducts used in the production of food, starch, ethanol or sugar.

Applicants identify herein a specific cellulase obtainable from *T. fusca*, known in the literature as E5, having a surprising array of characteristics which are especially beneficial in textile processing (specifically including denim stonewashing and bio-polishing), cleaning products and detergents, pulp and paper production, food processing and as an additive for animal feed. Specifically, Applicants have discovered that E5 has an especially broad pH/activity profile on insoluble substrate, being active in the pH range from about pH 5.0 to 10.5 with very little drop off in activity at the alkaline region. Moreover, E5 has significant activity levels at moderate pH and temperature, is stable for extended periods of time and at temperatures in excess of 80° C., is essentially insensitive to many buffer compositions and strengths, remains active after prolonged proteolytic cleavage, and is stable in the presence of oxidants such as perborate and perborate/TAED combinations and in detergents. Among the especially surprising features of E5 are its exceptional high pH activity on insoluble substrate such as cotton fabric compared to its activity on soluble substrate, which decreases significantly after its pH optimum of about 6.0. Thus, E5 is particularly well suited for high pH textile applications, such as simultaneous bleaching and bio-polishing or in laundry detergents and pre- or post-treatments which are formulated for a high pH. Another surprising feature is the ability of *T. fusca* to remain nearly unaffected by incubation in liquid detergent. An additional novel feature of the present invention is that truncated E5 also possesses many of the same exceptional characteristics as E5. For example, Applicants discovered that a truncated E5 enzyme can exhibit nearly identical surface fiber removal activity as E5.

The considerable advantages of the E5 or truncated E5 cellulase in industrial applications would not have been suggested by the prior art. The invention itself, together with further objects and attendant advantages, will best be understood by reference to the following detailed description taken in conjunction with the accompanying drawings.

BRIEF DESCRIPTION OF THE DRAWINGS

FIG. 1 illustrates the pH profile of E5 at 70° C. on soluble substrate.

FIG. 2 illustrates the activity of E5 from 40° C. to 80° C. soluble substrate.

FIG. 3 illustrates the stability of E5 at 20° C., 20 ppm at pH 8 and 10.

FIG. 4 illustrates the stability of E5 at 37° C., 20 ppm at pH 6, 8 and 10.

FIG. 5 illustrates the stability of E5 at 50° C., 20 ppm at pH 6, 8 and 10.

FIG. 6 illustrates the stability of E5 in the presence of perborate concentrations of 0 ppm, 90 ppm, 250 ppm, 500 ppm and 900 ppm.

FIG. 7 illustrates surface fiber removal of E5 at pH 6, pH 7.5, pH 8.5 and pH 9.5.

FIG. 8 illustrates the activity of E5 in the presence of protease at 50° C. and a pH of 7.

FIG. 9 illustrates the pH response of E5 compared to commercially available and heat treated Cheer® at 38° C.

FIG. 10 illustrates the pH response of E5 compared to commercially available and heat treated Cheer® at 60° C.

FIG. 11 illustrates the stability of E5 in Wisk® heavy duty liquid over 35 days compared to a representative cellulase from *T. longibrachiatum*.

DETAILED DESCRIPTION OF THE INVENTION

"Cotton-containing fabric" means sewn or unsewn fabrics, yarns or fibers made of pure cotton or cotton blends including cotton woven fabrics, cotton knits, cotton denims, cotton yarns, raw cotton and the like. When cotton blends are employed, the amount of cotton in the fabric is preferably at least about 35 percent by weight cotton. When employed as blends, the companion material employed in the fabric can include one or more non-cotton fibers including cellulosic or synthetic fibers such as polyamide fibers (for example, nylon 6 and nylon 66), acrylic fibers (for example, polyacrylonitrile fibers), and polyester fibers (for example, polyethylene terephthalate), polyvinyl alcohol fibers (for example, Vinylon), polyvinyl chloride fibers, polyvinylidene chloride fibers, polyurethane fibers, polyurea fibers and aramid fibers.

"Cellulose containing fabric" means any sewn or unsewn fabrics, yarns or fibers made of cotton or non-cotton containing cellulose or cotton or non-cotton containing cellulose blends including natural cellulosics and manmade cellulosics (such as jute, flax, ramie, rayon, and lyocell). Included under the heading of manmade cellulose containing fabrics are regenerated fabrics that are well known in the art such as rayon. Other manmade cellulose containing fabrics include chemically modified cellulose fibers (e.g, cellulose derivatized by acetate) and solvent-spun cellulose fibers (e.g. lyocell). Specifically included within the definition of cellulose containing fabric is any yarn or fiber made of such materials.

"Stonewashing composition" means a formulation for use in stonewashing cellulose containing fabrics. Stonewashing compositions are used to modify cellulose containing fabrics prior to presentation for consumer sale, i.e., during the manufacturing process. In contrast, detergent compositions are intended for the cleaning of soiled garments.

"Stonewashing" means the treatment of cellulose containing fabric with a cellulase solution under agitating and cascading conditions, i.e., in a rotary drum washing machine, to impart a "stonewashed" appearance to the denim. The cellulase solution according to the instant invention will functionally replace the use of stones in such art recognized methods, either completely or partially. Methods for imparting a stonewashed appearance to denim are described in U.S. Pat. No. 4,832,864 which is incorporated herein by reference in its entirety. Generally, stonewashing techniques have been applied to indigo dyed cotton denim.

"Detergent composition" means a mixture which is intended for use in a wash medium for the laundering of soiled cellulose containing fabrics. In the context of the present invention, such compositions may include, in addition to cellulases and surfactants, additional hydrolytic enzymes, builders, bleaching agents, bleach activators, bluing agents and fluorescent dyes, caking inhibitors, masking agents, cellulase activators, antioxidants, and solubilizers. Such compositions are generally used for cleaning soiled garments and are not used during the manufacturing process, in contrast to stonewashing compositions. Detergent compositions comprising cellulase are described in, for example, Clarkson et al., U.S. Pat. No. 5,290,474 and EP Publication No. 271 004, incorporated herein by reference.

"Derivative" means a protein which is derived from a precursor protein (e.g., the native protein) by addition of one or more amino acids to either or both the C- and N-terminal end, substitution of one or more amino acids at one or a number of different sites in the amino acid sequence, deletion of one or more amino acids at either or both ends of the protein or at one or more sites in the amino acid sequence, or insertion of one or more amino acids at one or more sites in the amino acid sequence. The preparation of an enzyme derivative is preferably achieved by modifying a DNA sequence which encodes for the native protein, transformation of that DNA sequence into a suitable host, and expression of the modified DNA sequence to form the derivative enzyme. The derivative of the invention includes peptides comprising altered amino acid sequences in comparison with a precursor enzyme amino acid sequence (e.g., a wild type or native state enzyme), which peptides retain a characteristic enzyme nature of the precursor enzyme but which have altered properties in some specific aspect. For example, an altered E5 or altered truncated E5 may have an increased pH optimum or increased temperature or oxidative stability but will retain its characteristic cellulolytic activity. Similarly, derivatives according to the present invention include a cellulose binding domain which has either been entirely removed, or modified in such a way so as to significantly impair its cellulose binding ability. It is contemplated that derivatives according to the present invention may be derived from a DNA fragment encoding an E5 or truncated E5 (as described below) wherein the functional activity of the expressed E5 derivative or truncated E5 is retained. For example, a DNA fragment encoding a truncated E5 may further include a DNA sequence or portion thereof encoding a hinge or linker attached to the truncated E5 DNA sequence at either the 5' or 3' end wherein the functional activity of the encoded truncated E5 domain is retained. Derivative further includes chemical modification to change the characteristics of the enzyme.

The term "truncated E5" refers to a protein comprising a derivative (usually shortened) of an intact E5 enzyme which retains cellulolytic activity. E5 in its intact form is believed to contain a catalytic core and a binding domain. The catalytic core and the cellulose binding domain may act together in a synergistic manner to effect efficient and often deleterious hydrolysis of cellulose fibers in a cellulose containing fabric often leading to undesirable strength loss. A truncated E5 lacking a functional binding domain may include other entities which do not include cellulose binding activity attributable to a cellulose binding domain. For example, the presence of a linker or hinge is specifically contemplated. Similarly, the covalent attachment of another enzymatic entity or a non-E5 cellulose binding domain to a truncated E5 is also specifically contemplated. It is expected that a truncated E5, or derivatives thereof according to the invention will retain at least 10% of the activity exhibited by E5 when each is assayed under similar conditions and dosed based on similar amounts of protein.

A truncated E5 may be made by any standard means of producing a truncated enzyme. Particularly effective means include the use of protease or chemical cleavage (i.e., cyanogen bromide) to cleave the enzyme, or the use of genetic engineering to directly express a truncated E5 in a microbial host. McGinnis et al., supra, suggest that *S. lividans* protease cleaved the 120 amino acids on the N-terminal of the E5 enzyme, leaving the remainder of the enzyme as a catalytically active core. Thus, one preferred embodiment of the present invention contemplates the use of a truncated E5 differing from E5 in that an N-terminal segment of the enzyme less than 121 amino acids in length is deleted, preferably differing from E5 in that the truncated E5 comprises the sequence of intact E5 starting at the threonine at residue 121. In another preferred embodiment of the present invention, a truncated E5 differs from E5 in that the amino acid sequence of E5 in the region of amino acids 1–120 has been altered to reduce or eliminate cellulose binding activity.

According to the present invention, a method of treating cellulosic material is provided comprising contacting the cellulosic material with a cellulase obtainable from *Thermomonospora fusca* corresponding to E5, a truncated E5, or a derivative thereof. In a process embodiment of the invention, the cellulosic material comprises cellulose containing fabric and the result of the method is to produce a stonewashed effect or an improvement in the feel and/or appearance of the fabric. In an alternative process embodiment of the invention, the cellulose containing fabric is contacted with an aqueous solution containing a detergent composition comprising a cellulase obtainable from *T. fusca* corresponding to E5, a truncated E5, or a derivative thereof. In yet another process embodiment of the invention, the cellulosic material comprises wood pulp and the addition of cellulase facilitates the production of paper products therefrom. In yet another process embodiment of the invention, the cellulosic material comprises animal feed and the method results in an increase in the digestibility or value of said animal feed. E5 as used herein refers to a cellulase having a molecular weight of about 45–47 kD (deduced from the amino acid sequence and confirmed by SDS-gel) and a pI of about 4.5–4.8 (as measured on IEF gel) and which is obtainable from *T. fusca*. *T. fusca* is a thermophilic, filamentous, actinomycete found in soil and common in rotting organic material such as decaying wood. The sequence of E5 is described in Lao et al., sypra. The cellulases according to the present invention may be produced by *T. fusca* by culturing under conditions which have been described in the literature so as to produce a fermentation broth from which E5 may be purified (see e.g., Walker et al., Biotechnol. Bioeng., vol. 40, pp. 1019–1026 (1992)). Alternatively, E5 may be produced by a microorganism which has been genetically modified to produce E5 or truncated E5 as in, for example, McGinnis et al., supra. As used herein, the cellulase is intended to encompass E5, truncated E5, or derivatives thereof. Preferably the truncated E5 comprises a catalytic domain and lacks significant cellulose binding activity.

In general, compositions comprising the cellulase according to the invention can be obtained by purification techniques based on the known characteristics and properties of the inventive cellulase. Specifically, where the cellulase according to the invention is part of a mixture of cellulases produced by the cultured organism, the entire cellulase mixture (whole cellulase) can be purified into substantially pure components by recognized separation techniques published in the literature, including ion exchange chromatography at a suitable pH, affinity chromatography and size exclusion. For example, in ion exchange chromatography (usually anion exchange chromatography), it is possible to separate the cellulase components by eluting with a pH gradient, or a salt gradient, or both a pH and a salt gradient. After purification, the requisite amount of the desired components could be recombined. Alternatively, genetic engineering techniques may be used to manipulate the produced cellulase mixtures, for example through the use of strains deleted in cellulase genes wherein the gene encoding the cellulase according to the invention is transformed and expressed by the otherwise cellulase deleted host strain.

Treatment of textiles according to the present invention contemplates textile processing or cleaning with a composition comprising a cellulase. Such treating includes, but is not limited to, stonewashing, modifying the texture, feel and/or appearance of cellulose containing fabrics or other techniques used during manufacturing or cleaning/reconditioning of cellulose containing fabrics. Additionally, treating within the context of this invention contemplates the removal of "immature" or "dead" cotton, from cellulosic fabric or fibers, i.e. immature cotton which is significantly more amorphous than mature cotton. Dead cotton is known to cause uneven dyeing and is undesirable. Accordingly, the composition contemplated in the present invention includes a cellulase component intended for use in washing of a soiled manufactured cellulose containing fabric. For example, cellulase may be used in a detergent composition for washing laundry. Detergent compositions useful in accordance with the present invention include special formulations such as pre-wash, pre-soak and home-use color restoration compositions. Such treating compositions, as described herein, may be in the form of a concentrate which requires dilution or in the form of a dilute solution or form which can be applied directly to the cellulose containing fabric. General treatment techniques known in the art for cellulase treatment of textiles are described in, for example, EP Publication No. 220 016 and GB Application Nos. 1,368,599 and 2,095,275.

Treatment of a cellulosic material according to the present invention further contemplates the treatment of animal feed, pulp and/or paper, food and grain for purposes known in the art. For example, cellulase is known to increase the value of animal feed, improve the drainability of wood pulp, enhance food products and reduce fiber in grain during the grain wet milling process or dry milling process.

According to a preferred embodiment of the present invention, the cellulase compositions described above may be employed as a stonewashing composition. Preferably, stonewashing according to the instant invention comprises preparing an aqueous solution which contains an effective amount of cellulase together with other optional ingredients including, for example, a buffer, a surfactant, and a scouring agent. An effective amount of cellulase enzyme composition is a concentration of cellulase enzyme sufficient for its intended purpose. Thus an "effective amount" of cellulase in the stonewashing composition according to the present invention is that amount which will provide the desired treatment, e.g., stonewashing. The amount of cellulase employed is also dependent on the equipment employed, the process parameters employed (the temperature of the cellulase treatment solution, the exposure time to the cellulase solution, and the like), and the cellulase activity (e.g., a particular solution will require a lower concentration of cellulase where a more active cellulase composition is used as compared to a less active cellulase composition). The exact concentration of cellulase in the aqueous treatment solution to which the fabric to be stonewashed is added can be readily determined by the skilled artisan based on the above factors as well as the desired result. Preferably the cellulase is present in a concentration of from 1 to 5,000 ppm and most preferably 10 to 200 ppm total protein.

Optionally, a buffer is employed in the stonewashing composition such that the concentration of buffer is sufficient to maintain the pH of the solution within the range wherein the employed cellulase exhibits activity which, in turn, depends on the nature of the cellulase employed. The exact concentration of buffer employed will depend on several factors which the skilled artisan can readily take into account. For example, in a preferred embodiment, the buffer as well as the buffer concentration are selected so as to maintain the pH of the final cellulase solution within the pH range required for optimal cellulase activity. Because E5 has a broad pH profile from about 5.0 through about 10.5 on insoluble substrate, the cellulase may be used in either mildly acidic, neutral or alkaline pH with optimal activity, depending on the specific needs of the textile processor. Suitable buffers at pH within the activity range of E5 are well known to those skilled in the art in the field.

In addition to cellulase and a buffer, the stonewashing composition may optionally contain a surfactant. Suitable surfactants include any surfactant compatible with the cellulase and the fabric including, for example, anionic, nonionic and ampholytic surfactants. Suitable anionic surfactants for use herein include linear or branched alkylbenzenesulfonates; alkyl or alkenyl ether sulfates having linear or branched alkyl groups or alkenyl groups; alkyl or alkenyl sulfates; olefinsulfonates; alkanesulfonates and the like. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyalkylene ethers, as well as higher fatty acid alkanolamides or alkylene oxide adduct thereof, and fatty acid glycerine monoesters. Mixtures of surfactants can also be employed in manners known to those skilled in the art.

In a preferred embodiment, a concentrated stonewashing composition can be prepared for use in the methods described herein. Such concentrates would contain concentrated amounts of the cellulase composition described above, buffer and surfactant, preferably in an aqueous solution. When so formulated, the stonewashing concentrate can readily be diluted with water so as to quickly and accurately prepare stonewashing compositions according to the present invention and having the requisite concentration of these additives. When aqueous concentrates are formulated, these concentrates can be diluted so as to arrive at the requisite concentration of the components in the cellulase solution as indicated above. As is readily apparent, such stonewashing concentrates will permit facile formulation of the cellulase solutions as well as permit feasible transportation of the concentration to the location where it will be used. The stonewashing concentrate can be in any art recognized form, for example, liquid, emulsion, gel, or paste. Such forms are well known to those skied in the art.

When a solid stonewashing concentrate is employed, the cellulase composition may be a granule, a powder, an agglomerate or a solid disk. When granules are used, the granules are preferably formulated so as to contain a cellulase protecting agent. See, for example, U.S. Ser. No. 07/642,669, filed Jan. 17, 1991 as Attorney Docket No. 010055-073 and entitled "GRANULES CONTAINING BOTH AN ENZYME AND AN ENZYME PROTECTING AGENT AND DETERGENT COMPOSITIONS CONTAINING SUCH GRANULES," which application is incorporated herein by reference in its entirety. Likewise, the granules can be formulated so as to contain materials to reduce the rate of dissolution of the granules into the wash medium. Such materials and granules are disclosed in U.S. Pat. No. 5,254,283 which is incorporated herein by reference in its entirety.

Other materials can also be used with or placed in the stonewashing composition of the present invention as desired, including stones, pumice, fillers, solvents, enzyme activators, and anti-redeposition agents.

The cellulose containing fabric is contacted with the stonewashing composition containing an effective amount of the cellulase by intermingling the treating composition with the stonewashing composition, and thus bringing the cellulase enzyme into proximity with the fabric. Subsequently, the aqueous solution containing the cellulase and the fabric is agitated. If the treating composition is an aqueous solution, the fabric may be directly soaked in the solution. Similarly, where the stonewashing composition is a concentrate, the concentrate is diluted into a water bath with the cellulose containing fabric. When the stonewashing composition is in a solid form, for example a pre-wash gel or solid stick, the stonewashing composition may be contacted by directly applying the composition to the fabric or to the wash liquor.

The cellulose containing fabric is incubated with the stonewashing solution under conditions effective to allow the enzymatic action to confer a stonewashed appearance to the cellulose containing fabric. For example, during stonewashing, the pH, liquor ratio, temperature and reaction time may be adjusted to optimize the conditions under which the stonewashing composition acts. "Effective conditions" necessarily refers to the pH, liquor ratio, and temperature which allow the cellulase enzyme to react efficiently with cellulose containing fabric. The reaction conditions effective for the stonewashing compositions of the present invention are substantially similar to well known methods used with corresponding prior art cellulase compositions. Accordingly, it is within the skill of those in the art to maximize conditions for using the stonewashing compositions according to the present invention.

The liquor ratios during stonewashing, i.e., the ratio of weight of stonewashing composition solution (i.e., the wash liquor) to the weight of fabric, employed herein is generally an amount sufficient to achieve the desired stonewashing effect in the denim fabric and is dependent upon the process used. Preferably, the liquor ratios are from about 4:1 to about 50:1; more preferably from 5:1 to about 20:1, and most preferably from about 10:1 to about 15:1.

Reaction temperatures during stonewashing with the present stonewashing compositions are governed by two competing factors. Firstly, higher temperatures generally correspond to enhanced reaction kinetics, i.e., faster reactions, which permit reduced reaction times as compared to reaction times required at lower temperatures. Accordingly, reaction temperatures are generally at least about 10° C. and greater. Secondly, cellulase is a protein which loses activity beyond a given reaction temperature, which temperature is dependent on the nature of the cellulase used. Thus, if the reaction temperature is permitted to go too high, the cellulolytic activity is lost as a result of the denaturing of the cellulase. Because E5 shows excellent thermostability, the temperature of the stonewash may be quite high, i.e., greater than 80° C. if necessary. However, standard temperatures in the art are generally in the range of 35° C. to 65° C. which will also be suitable for the cellulase of the invention.

Reaction times are dependent on the specific conditions under which the stonewashing occurs. For example, pH, temperature and concentration of cellulase will all effect the optimal reaction time. Generally, reaction times are from about 5 minutes to about 5 hours, and preferably from about 10 minutes to about 3 hours and, more preferably, from about 20 minutes to about 1 hour.

According to yet another preferred embodiment of the present invention, the cellulase compositions described above may be employed in a detergent composition. The detergent compositions according to the present invention are useful as pre-wash compositions, pre-soak compositions, or for cleaning during the regular wash or rinse cycle. Preferably, the detergent composition of the present invention comprises an effective amount of cellulase, a surfactant, and optionally include other ingredients described below.

An effective amount of cellulase employed in the detergent compositions of this invention is an amount sufficient to impart the desirable effects known to be produced by cellulase on cellulose containing fabrics, for example, depilling, softening, anti-pilling, surface fiber removal and cleaning. Preferably, the cellulase in the detergent composition is employed in a concentration of about 10 ppm to about 20,000 ppm of detergent.

The concentration of cellulase enzyme employed in the detergent composition is preferably selected so that upon dilution into a wash medium, the concentration of cellulase enzyme is in a range of about 0.01 to about 1000 ppm, preferably from about 0.02 ppm to about 500 ppm, and most preferably from about 0.5 ppm to about 250 ppm total protein. The amount of cellulase enzyme employed in the detergent composition will depend on the extent to which the detergent will be diluted upon addition to water so as to form a wash solution.

The detergent compositions of the present invention may be in any art recognized form, for example, as a liquid diluent, in granules, in emulsions, in gels, or in pastes. Such forms are well known to the skilled artisan. When a solid detergent composition is employed, the cellulase is preferably formulated as granules. Preferably, the granules can be formulated so as to additionally contain a cellulase protecting agent. See, for instance, U.S. Ser. No. 07/642,669 filed Jan. 17, 1991 abandoned as and entitled "GRANULES CONTAINING BOTH AN ENZYME AND AN ENZYME PROTECTING AGENT AND DETERGENT COMPOSITIONS CONTAINING SUCH GRANULES" which application is incorporated herein by reference in its entirety. Likewise, the granule can be formulated so as to contain materials to reduce the rate of dissolution of the granule into the wash medium. Such materials and granules are disclosed in U.S. Pat. No. 5,254,283 which is incorporated herein by reference in its entirety.

The detergent compositions of this invention employ a surface active agent, i.e., surfactant, including anionic, nonionic and ampholytic surfactants well known for their use in detergent compositions.

Suitable anionic surfactants for use in the detergent composition of this invention include linear or branched alkylbenzenesulfonates; alkyl or alkenyl ether sulfates having linear or branched alkyl groups or alkenyl groups; alkyl or alkenyl sulfates; olefinsulfonates; and alkanesul-fonates. Suitable counter ions for anionic surfactants include alkali metal ions such as sodium and potassium; alkaline earth metal ions such as calcium and magnesium; ammonium ion; and alkanolamines having 1 to 3 alkanol groups of carbon number 2 or 3. Ampholytic surfactants include quaternary ammonium salt sulfonates, and betaine-type ampholytic surfactants. Such ampholytic surfactants have both the positive and negative charged groups in the same molecule. Nonionic surfactants generally comprise polyoxyal-kylene ethers, as well as higher fatty acid alkanolamides or alkylene oxide adduct thereof, fatty acid glycerine monoesters, and the like. Suitable surfactants for use in this invention are disclosed in British Patent Application No. 2 094 826 A, the disclosure of which is incorporated herein by reference. Mixtures of such surfactants can also be used. The surfactant or a mixture of surfactants is generally employed in the detergent compositions of this invention in an amount from about 1 weight percent to about 95 weight percent of the total detergent composition and preferably from about 5 weight percent to about 45 weight percent of the total detergent composition. In addition to the cellulase composition and the surfactant(s), the detergent compositions of this invention can optionally contain one or more of the following components:

Hydrolases Except Cellulase

Suitable hydrolases include carboxylate ester hydrolase, thioester hydrolase, phosphate monoester hydrolase, and phosphate diester hydrolase which act on the ester bond; glycoside hydrolase which acts on glycosyl compounds; an enzyme that hydrolyzes N-glycosyl compounds; thioether hydrolase which acts on the ether bond; and a-amino-acyl-peptide hydrolase, peptidyl-amino acid hydrolase, acyl-amino acid hydrolase, dipeptide hydrolase, and peptidyl-peptide hydrolase which act on the peptide bond. Preferable among them are carboxylate ester hydrolase, glycoside hydrolase, and peptidyl-peptide hydrolase. Suitable hydrolases include (1) proteases belonging to peptidyl-peptide hydrolase such as pepsin, pepsin B, rennin, trypsin, chymotrypsin A, chymotrypsin B, elastase, enterokinase, cathepsin C, papain, chymopapain, ficin, thrombin, fibrinolysin, renin, subtilisin, aspergillopeptidase A, collagenase, clostridiopeptidase B, kallikrein, gastrisin, cathepsin D., bromelin, keratinase, chymotrypsin C, pepsin C, aspergillopeptidase B, urokinase, carboxypeptidase A and B, and aminopeptidase; (2) glycoside hydrolases (cellulase which is an essential ingredient is excluded from this group) α-amylase, β-amylase, gluco amylase, invertase, lysozyme, pectinase, chitinase, and dextranase. Preferably among them are α-amylase and β-amylase. They function in acid to neutral systems, but one which is obtained from bacteria exhibits high activity in an alkaline system; (3) carboxylate ester hydrolase including carboxyl esterase, lipase, pectin esterase, and chlorophyllase. Especially effective among them is lipase.

The hydrolase other than cellulase is incorporated into the detergent composition as much as required according to the purpose. It should preferably be incorporated in an amount of 0.001 to 5 weight percent, and more preferably 0.02 to 3 weight percent, in terms of purified protein. This enzyme should be used in the form of granules made of crude enzyme alone or in combination with other components in the detergent composition. Granules of crude enzyme are used in such an amount that the purified enzyme is 0.001 to 50 weight percent in the granules. The granules are used in an amount of 0.002 to 20 and preferably 0.1 to 10 weight percent. As with cellulases, these granules can be formulated so as to contain an enzyme protecting agent and a dissolution retardant material.

Cationic Surfactants and Long-Chain Fatty Acid Salts

Such cationic surfactants and long-chain fatty acid salts include saturated or unsaturated fatty acid salts, alkyl or alkenyl ether carboxylic acid salts, a-sulfofatty acid salts or esters, amino acid-type surfactants, phosphate ester surfactants, quaternary ammonium salts including those having 3 to 4 alkyl substituents and up to 1 phenyl substituted alkyl substituents. Suitable cationic surfactants and long-chain fatty acid salts are disclosed in British Patent Application No. 2 094 826 A, the disclosure of which is incorporated herein by reference. The composition may contain from about 1 to about 20 weight percent of such cationic surfactants and long-chain fatty acid salts.

Builders

A. Divalent Sequestering Agents

The composition may contain from about 0 to about 50 weight percent of one or more builder components selected from the group consisting of alkali metal salts and alkanolamine salts of the following compounds: phosphates, phosphonates, phosphonocarboxylates, salts of amino acids, aminopolyacetates high molecular electrolytes, non-dissociating polymers, salts of dicarboxylic acids, and aluminosilicate salts. Suitable divalent sequestering gents are disclosed in British Patent Application No. 2 094 826 A, the disclosure of which is incorporated herein by reference.

B. Alkalis or Inorganic Electrolytes

The composition may contain from about 1 to about 50 weight percent, preferably from about 5 to about 30 weight percent, based on the composition of one or more alkali metal salts of the following compounds as the alkalis or inorganic electrolytes: silicates, carbonates and sulfates as well as organic alkalis such as triethanolamine, diethanolamine, monoethanolamine and triisopropanolamine.

Antiredeposition Agents

The composition may contain from about 0.1 to about 5 weight percent of one or more of the following compounds as antiredeposition agents: polyethylene glycol, polyvinyl alcohol, polyvinylpyrrolidone and carboxymethylcellulose.

Among them, a combination of carboxymethyl-cellulose and/or polyethylene glycol with the cellulase composition of the present invention provides for an especially useful dirt removing composition.

Bleaching Agents

The use of the cellulase of the present invention in combination with a bleaching agent such as potassium monopersulfate, sodium percarbonate, sodium perborate, sodium sulfate/hydrogen peroxide adduct and sodium chloride/hydrogen peroxide adduct or/and a photo-sensitive bleaching dye such as zinc or aluminum salt of sulfonated phthalocyanine further improves the detergenting effects. Similarly, bleaching agents and bleach catalysts as described in EP 684 304 may be used.

Bluing Agents and Fluorescent Dyes

Various bluing agents and fluorescent dyes may be incorporated in the composition, if necessary. Suitable bluing agents and fluorescent dyes are disclosed in British Patent Application No. 2 094 826 A, the disclosure of which is incorporated herein by reference.

Caking Inhibitors

The following caking inhibitors may be incorporated in the powdery detergent: p-toluenesulfonic acid salts, xylenesulfonic acid salts, acetic acid salts, sulfosuccinic acid salts, talc, finely pulverized silica, amorphous silicas, clay, calcium silicate (such as Micro-Cell of Johns Manville Co.), calcium carbonate and magnesium oxide.

Masking Agents for Factors Inhibiting the Cellulase Activity

The cellulase composition of this invention are deactivated in some cases in the presence of copper, zinc, chromium, mercury, lead, manganese or silver ions or their compounds. Various metal chelating agents and metal-precipitating agents are effective against these inhibitors. They include, for example, divalent metal ion sequestering agents as listed in the above item with reference to optional additives as well as magnesium silicate and magnesium sulfate.

Cellobiose, glucose and gluconolactone act sometimes as inhibitors. It is preferred to avoid the co-presence of these saccharides with the cellulase as far as possible. In case the co-presence in unavoidable, it is necessary to avoid the direct contact of the saccharides with the cellulase by, for example, coating them.

Long-chain-fatty acid salts and cationic surfactants act as the inhibitors in some cases. However, the co-presence of these substances with the cellulase is allowable if the direct contact of them is prevented by some means such as tableting or coating.

The above-mentioned masking agents and methods may be employed, if necessary, in the present invention.

Cellulase-Activators

The activators vary depending on variety of the cellulases. In the presence of proteins, cobalt and its salts, magnesium and its salts, and calcium and its salts, potassium and its salts, sodium and its salts or monosaccharides such as mannose and xylose, the cellulases are activated and their derging powers are improved remarkably.

Antioxidants

The antioxidants include, for example, tert-butyl-hydroxytoluene, 4,4'-butylidenebis(6-tert-butyl-3-methylphenol), 2,2'-butylidenebis(6-tert-butyl-4-methylphenol), monostyrenated cresol, distyrenated cresol, monostyrenated phenol, distyrenated phenol and 1,1 -bis(4-hydroxy-phenyl)cyclohexane.

Solubilizers

The solubilizers include, for example, lower alcohols such as ethanol, benzenesulfonate salts, lower alkylbenzene-sulfonate salts such as p-toluenesulfonate salts, glycols such as propylene glycol, acetylbenzene-sulfonate salts, acetamides, pyridinedicarboxylic acid amides, benzoate salts and urea.

The detergent composition of the present invention can be used in a broad pH range from acidic to alkaline pH. In a preferred embodiment, the detergent composition of the present invention can be used in mildly acidic, neutral or alkaline detergent wash media having a pH of from above 5 to no more than about 12.

Aside from the above ingredients, perfumes, buffers, preservatives, dyes and the like can be used, if desired, with the detergent compositions of this invention. Such components are conventionally employed in amounts heretofore used in the art.

When a detergent base used in the present invention is in the form of a powder, it may be one which is prepared by any known preparation methods including a spray-drying method and a granulation method. The detergent base obtained particularly by the spray-drying method, agglomeration method, dry mixing method or non-tower route methods are preferred. The detergent base obtained by the spray-drying method is not restricted with respect to preparation conditions. The detergent base obtained by the spray-drying method is hollow granules which are obtained by spraying an aqueous slurry of heat-resistant ingredients, such as surface active agents and builders, into a hot space. After the spray-drying, perfumes, enzymes, bleaching agents, inorganic alkaline builders may be added. With a highly dense, granular detergent base obtained such as by the spray-drying-granulation or agglomeration method, various ingredients may also be added after the preparation of the base.

When the detergent base is a liquid, it may be either a homogeneous solution or an inhomogeneous dispersion. For removing the decomposition of carboxymethylcellulose by the cellulase in the detergent, it is desirable that carboxymethylcellulose is granulated or coated before the incorporation in the composition.

The detergent compositions of this invention may be incubated with cellulose containing fabric, for example soiled fabrics, in industrial and household uses at temperatures, reaction times and liquor ratios conventionally employed in these environments. The incubation conditions, i.e., the conditions effective for treating cellulose containing fabrics with detergent compositions according to the present invention, will be readily ascertainable by those of skill in the art. Accordingly, the appropriate conditions effective for treatment with the present detergents will correspond to those using similar detergent compositions which include known cellulases.

Detergents according to the present invention may additionally be formulated as a pre-wash in the appropriate solution at an intermediate pH where sufficient activity exists to provide desired improvements softening, depilling, pilling prevention, surface fiber removal or cleaning. When the detergent composition is a pre-soak (e.g., pre-wash or pre-treatment) composition, either as a liquid, spray, gel or paste composition, the truncated cellulase enzyme is generally employed from about 0.0001 to about 1 weight percent based on the total weight of the pre-soak or pre-treatment composition. In such compositions, a surfactant may optionally be employed and when employed, is generally present at a concentration of from about 0.005 to about 20 weight percent based on the total weight of the pre-soak. The remainder of the composition comprises conventional components used in the pre-soak, i.e., diluent, buffers, other enzymes (proteases), and the like at their conventional concentrations.

It is contemplated that compositions comprising truncated cellulase enzymes described herein can be used in home use as a stand alone composition suitable for restoring color to faded fabrics (see, for example, U.S. Pat. No. 4,738,682, which is incorporated herein by reference in its entirety) as well as used in a spot-remover and for depilling and antipilling (pilling prevention).

The use of the cellulase according to the invention may be particularly effective in feed additives and in the processing of pulp and paper. These additional industrial applications are described in, for example, PCT Publication No. 95/16360 and Finnish Granted Patent No. 87372, respectively.

In order to further illustrate the present invention and advantages thereof, the following specific examples are given with the understanding that they are being offered to illustrate the present invention and should not be construed in any way as limiting its scope.

EXAMPLES

Examile 1

Production and Purification of E5

Clones prepared as in McGinnis et al., Biotechnology, vol. 32, pp. 8157–8161 (1993) may be used to express E5 in *Streptomyces lividans* and should be grown under conditions suitable for expression of the plasmid. E5 enzyme may then be purified from the resulting fermentation supernatant according to the procedure recited in Walker et al., Biotechnol. Bioeng., vol. 40, pp. 101 9–1026 (1992) and Irwin et al. *Biotechnology and Bioengineering* ibid. vol. 42, pp. 1002–1013 (1993). Alternatively, E5 paste can be solubilized in MOPS, pH 7, spun down and the supernatant saved (crude E5) is prepared. A second resolubilization and spinning is done on the loose pellet. The combined recovery is around 75%. The supernatant is precipitated with 0.65 M ammonium sulfate in the cold room with stirring and then centrifuged (14,000 rpm for 20 min in the SS-34 rotor). The pellet is resolubilized in a buffer containing 0.25 M ammonium sulfate, 5 mM $KP_i$ pH 6.0. To remove antifoam (to make filtration less difficult) the solution is warmed to room temperature and centrifuged (15,000 rpm for 30 min in the SS-34 rotor). The white film is removed off the top and the mixture filtered through a 0.45 micron membrane using a disposable filtering device under vacuum. A phenyl sepharose column is pre-equilibrated with 0.25 M ammonium sulfate, 5 mM $KP_i$, pH 6. The filtered E5 is loaded and then washed with the equilibration buffer until the flow-through absorbance returned to a low level. The column is then washed with one volume of 0.125 M ammonium sulfate, 5 mM $KP_i$, pH 6 (little absorbance is observed). The E5 is eluted with 5 mM $KP_i$, pH 6; small fractions are collected. After the absorbance returned to background, the column is then eluted with water and fractions collected. Small aliquots from each fraction of possible interest are concentrated in spin columns, washed with water, and concentrated 3–4x. The fractions are then analyzed by IEF gel. The purest fractions are those near the end of the 5 mM KPi elution and at the beginning of the water elution. On both a small column (25 ml) and a larger one (450 ml), the yield of activity from pooling the purest fractions obtained through the above procedure was 30% overall. These fractions were either one band on silver stained IEF, or additionally contained about two minor bands.

Activity levels were assayed as follows: Add 5 to 20 $\mu$l of an appropriate enzyme solution at a concentration sufficient to provide a requisite amount of enzyme in the final solution. Add 250 $\mu$l of 2 weight percent RBB-CMC (Remazol Brilliant Blue R-Carboxymethyl cellulose—commercially available from Mega Zyme, North Rocks, Australia) in 50 mm sodium acetate buffer at pH 5.5. Vortex and incubate at 40° C. for 30 minutes. Chill in an ice bath for 5–10 minutes. Add 1000 $\mu$l of 80% ethanol containing 0.3M sodium acetate and 0.02M zinc acetate. Vortex and let sit for 5–10 minutes. Centrifuge and pour supernatant into cuvettes. Measure the optical density of the solution in each cuvette at 590 nm. Higher levels of optical density correspond to higher levels of enzyme activity. Protein determinations were done using the BCA method with BSA as the standard according to the distributors instructions (Pierce, BCA Protein Assay Reagent, Prod. No. 23225). The specific activity of crude E5 (resolubilized paste) was determined to be about 1.6 units/mg protein. Purified E5 has a specific activity of about 11 units/mg.

Example 2

Protease Treatment of E5 to Produce Truncated E5

Intact E5, solubilized and purified as in Example 1, was treated with several proteases to yield variant truncated E5. Five proteases, Alcalase (available from Novo Nordisk, Denmark), Purafect (available from Genencor International, Inc.) and three different mutant bacterial proteases (BA, B1 and B2) each having distinct catalytic behavior were used to provide a variety of different cleavage patterns in E5. A concentration of either 0.5 or 5 mg/ml E5 was incubated with 2.5 mg/ml of protease. Incubations were done at pH 5 (NaOAc buffer), 7 (TES buffer) and 9 (glycine buffer) at 20, 37 and 50° C. A final concentration of 15 gpg (grains per gallon) $Ca^{+2}$ was added. Aliquots were removed at 0, 15 min, 30 min, 45 min, 1 hour, 2 hours, 4 hours, 8 hours and 24 hours and immediately frozen. The protease treated aliquots were analyzed by IEF gels (Coomassie staining) and for activity on RBB-CMC as in Example 1.

During the course of all the incubations, two new bands with slightly higher pl's than E5 appeared when analyzed by IEF. An overlay using RBB-CMC demonstrated that at least one of these bands always had activity. Alcalase produced bands from E5 in the quickest time and thus had the greatest effect on E5. For example, given a concentration of 1:5 E5:Alcalase (measured in mg protein/ml) at 37° C. and pH 7 and 9, all three bands on an IEF gel are formed after 30 min, and the highest pl band is predominant after 8 hours. The other proteases were less aggressive. Purafect at pH 5 produced only faint activity towards E5 at 37° C. At pH 7 and 9, at least 2 hours incubation were required before any significant development of the high pi band. BA and B1 appeared to effect E5 less than Alcalase and Purafect and required at least 4 hours incubation before significant development of the high pl band. BA digests E5 to the other bands, but may also further degrade E5 (the bands become very light). Digestions with 1:1 E5:protease (measured in mg protein/ml were done at 37° C. and pH 9 with Purafect, B2 and Alcalase. Once again, Alcalase digested E5 the fastest, to one band after 8 hours. With Purafect and B2, both of the new bands are present after 30 hours, showing that these proteases digest E5 slower than does Alcalase.

The stability of E5 with Purafect against time is shown in FIG. 8. As shown in FIG. 8, E5 retains a significant portion of its original activity on RBB-CMC after over 25 hours at 50° C., pH 7. In addition, each of the other protease treated E5 mixtures retained at least 50% of their activity.

Example 3

Temperature Stability, PH Stability, Storage Stability and Oxidative Stability of E5

The pH profile of E5 was determined by incubating separate aliquots of crude E5 with RBB-CMC at 70° C. for 30 minutes. A citrate-phosphate buffer was used from pH 4–9 and a glycine buffer was used from pH 9–11. Activity was determined by measuring the absorbance at 620 nm and the results shown in FIG. 1. As shown in FIG. 1, E5 has a pH optimum on RBB-CMC of about 6.

Separate aliquots of crude E5 were incubated at pH 5.5 in 0.05M sodium acetate buffer for 30 minutes with RBB-CMC at varying temperatures between 40° C. and 80° C. and the activity determined by measuring the absorbance at 590 nm. The results are provided in FIG. 2. As shown in FIG. 2, E5 shows a temperature optimum in the range of 70–75 C.

The pH stability of E5 over extended periods of time was measured at a dilute concentration (20 ppm) at 20° C., 37° C. and 50° C. at pH's of 6 (50 mM MOPS buffer), 8 (50 mM MOPS buffer) and 10 (50 mM glycine buffer). Over the course of nine days, aliquots were removed and assayed using the RBB-CMC activity assay described in Example 1. The results are shown in FIGS. 3–5. As shown in FIGS. 3–5, at 37° C. and 50° C. and pH 6, at least 60–70% of the activity remains after nine days. At pH 8, none of the incubations showed greater than 20% loss in activity after nine days and at pH 10, there was no significant loss in activity at 20° C. and 37° C., while the incubation at 50° C. lost 50% of its activity after nine days. As can be seen from the results shown in FIGS. 3–5, E5 is very stable at each of the conditions tested for extended periods of time.

The oxidative stability of E5 was tested by preincubating 15 ppm crude E5 with 90 to 900 ppm perborate in MOPS buffer (pH 7) at 40° C. Aliquots were removed over a 30 min period and assayed by RBB-CMC for activity as in Example 1. There was no detectable loss of activity compared to the control in any of the incubations (FIG. 6). By comparison, EGIII from *Trichoderma longibrachiatum* is completely inactivated by approximately 500 ppm perborate +170 ppm TAED at pH 5.5 and 50° C.

E5 activity in the presence of perborate was also tested by surface fiber removal studies in a launderometer. The test was performed by contacting the crude cellulase at 60° C. for one hour at pH 9 (glycine buffer) with cotton swatches. Results indicate that there may be a small loss of activity with perborate, but it is not dependent on perborate concentration. Even the incubation with 900 ppm perborate showed good surface fiber removal. The control of 900 ppm perborate without enzyme showed minor surface fiber removal.

Example 4

Effect of Various Buffers on E5 Activity

E5 was incubated with RBB-CMC with a variety of buffers at varying pH to determine the effect on activity of each buffer. Each buffer was tested at 20, 100 and 200 mM. At pH 5, citrate, succinate and sodium acetate were used; at pH 7, phosphate, MOPS and TES were used; and at pH 9, borate and CHES were used. The solutions containing E5 buffer and RBB-CMC were incubated for 30 minutes at 40° C. and then analyzed for cellulase activity as described in Example 1. Activity was standardized to the 20 mM buffer concentration under each buffer condition.

As shown in Table 1 below, E5 proved relatively insensitive to the buffers or concentrations used.

TABLE 1

Buffer Conc, mM

Activity at pH 5

| | Sodium Acetate | Citrate | Succinate |
|---|---|---|---|
| 20 | 100 | 100 | 100 |
| 100 | 84 | 87 | 95 |
| 200 | 78 | 65 | 88 |

Activity at pH 7

| | MOPS | Potassium Phosphate | TES |
|---|---|---|---|
| 20 | 100 | 100 | 100 |
| 100 | 127 | 118 | 120 |
| 200 | 129 | 83 | 117 |

Activity at pH 9

| | Borate | CHES |
|---|---|---|
| 20 | 100 | 100 |
| 100 | 100 | 113 |
| 200 | 130 | 129 |

Example 5

Surface Fiber Removal For E5 and Protease Treated E5

E5 was tested using 100, 300, 500 and 1000 RBB-CMC units in 400 ml of buffer at pH 6, 7.5, 8.5 and 9.5 at 60° C. A dose response is observed, with excellent SFR activity observed at either 500 or 1000 units. E5 is optimally active in a broad range extending at least from around pH 6.0 to pH 9.5. These results are summarized in FIG. 7. As shown in FIG. 7, the pH profile for E5 with insoluble substrate differs considerably from the pH profile for E5 with RBB-CMC in FIG. 1.

Two sets of launderometer studies were performed with E5, all tests comprising 350 units of cellulase in the launderometer. In the first, the E5 was preincubated with protease prior to adding to the launderometer. The two representative proteases chosen were Purafect and Alcalase. For pre-incubation, 40 mg protease (1000 ppm, resulting in 100 ppm after dilution in the launderometer) was mixed with the cellulase and let stand for 20 hours at 37° C. and pH 9 (glycine buffer) with 15 ppm calcium. The conditions used have been established by Applicants as sufficient to cleave E5 to a truncated E5 protein. One control was prepared with E5 which had been preincubated without protease and a second control was prepared with buffer alone (no enzyme added). The launderometer study was done with the pre-incubated mixture at 60° C. for 1 hour at pH 9 (glycine buffer) on cotton swatches. The jeans were then dried in a clothes drier and graded by a panel of 4 evaluators. The grade scale for surface fiber removal ranged from 1 (most surface fuzz) to 5 (least surface fuzz). The results are shown in Table 2. As shown in Table 2, E5 samples pre-incubated with either protease showed no significant loss in surface fiber removal activity compared to the E5 incubated without protease.

TABLE 2

| Treatment | Average Score |
|---|---|
| E5 no added protease, preincubated | 3 |
| E5 + Purafect, preincubated | 2.5 |
| E5 + Alcalase, preincubated | 3 |
| Buffer | 1 |

In the second set of launderometer studies, the E5 samples were not pretreated, but were added to the launderometer with 1, 10 or 50 ppm of either Purafect of Alcalase. Control experiments provided comparative results for E5 with no protease, EGII (*Trichoderma longibrachiatum*) cellulase without protease, buffer, and either Alcalase or Purafect alone. The results are shown in Table 3. As shown in Table 3, panel rating of the swatches treated with E5 and protease showed only minor reduction in surface fiber removal compared to E5 without protease.

TABLE 3

| Treatment | Average Score |
|---|---|
| Purafect | 1.25 |
| Alcalase | 1.5 |
| E5 + 1 ppm Purafect | 3.75 |
| E5 + 10 ppm Purafect | 4.25 |
| E5 + 50 ppm Purafect | 4.25 |
| E5 + 1 ppm Alcalase | 4.75 |
| E5 + 10 ppm Alcalase | 3.25 |
| E5 + 50 ppm Alcalase | 4 |
| E5 + 15 gpg Calcium | 4.75 |
| E5 | 5 |
| EGII | 4.5 |
| Buffer | 1 |

As established above, E5 is digested by proteases to a truncated protein that has excellent activity both on RBB-CMC (see FIG. 8) and on cotton surface fibers. This is especially apparent in the launderometer test, which shows that E5 is active even in the presence of a high level of protease during a 1 hour incubation with swatch.

Example 6
Denim Abrasion with E5 and Truncated E5

Crude E5 was tested for abrasion performance on denim to determine the effectiveness of E5 in stonewashing applications. Stonewashing experiments were performed in a Unimac. Enzyme (13,500 RBB-CMC units of E5 or truncated E5 made by incubation with Alcalase) was added to the solution, which contained 20 mM MOPS, 9.5 g of Triton X-100, pH 7.0, and eight previously desized denim jean legs. The temperature was 60° C. Four jeans were removed after 60 minutes and rinsed in cold water. They were returned to the Unimac 30 minutes later. At this time, a detergent post-wash was done at 70° C. using 50 g of detergent. The jeans were then dried in a clothes drier and graded by a panel of evaluators. The grade scale is a panel of denim swatches ranging in abrasion from 1 (no abrasion) to 10 (very abraded).

TABLE 4

| E5 abrasion | |
|---|---|
| Abrasion Time (min.) | Abrasion Level |
| 60 | 5.5 |
| 90 | 7 |

TABLE 5

| E5 core abrasion | |
|---|---|
| Abrasion Time (min.) | Abrasion |
| 60 | 5.5 |
| 90 | 7 |

As can be seen from Tables 4 and 5, E5 has excellent abrasion levels after both 60 and 90 minutes. More surprisingly, in this example the abrasion is not reduced upon truncation of the enzyme.

Example 7
Simultaneous Desize and Bleach

Twelve sized jeans were used to demonstrate the efficacy of E5 in a simultaneous desize and bleach process. The jeans were combined in a solution having a final buffer concentration of 40 mM MOPS, pH 7 and also containing 10g of Triton X-100. To this was added 14,000 units of crude E5 and 5 ml of *Bacillus licheniformis* derived α-amylase, and the cycle run at 65° C. and 36 rpm. Half of the jeans were removed after 30 min and rinsed in cold water, while the others continued until 60 min. No detergent post-wash was done. After drying, the jeans were graded by a panel of evaluators. The grade scale is a panel of denim swatches ranging in abrasion from 1 (no abrasion) to 10 (very abraded).

TABLE 6

| Time (min) | Abrasion |
|---|---|
| 30 | 4 |
| 60 | 5.5 |

Surprisingly, the amount of abrasion and the pattern are similar to that obtained from jeans which have been first desized before the E5 stonewash (see, e.g., Example 6).

Example 8
Performance of E5 in Detergents

Evaluation of surface fiber removal from cotton swatches with E5 were conducted in a Terg-O-Tometer under conditions including a temperature of 100° F. or 140° C. for a 2.5 hour wash cycle at 125 rpm agitation speed and 150 ppm water hardness ($CaCO_3$). 8 swatches (4 knit, 4 woven) were loaded per test beaker. Two types of fabric were tested: a cotton interlock knit material obtained from Burlington Mills in North Carolina, and woven cotton material, style 400, from Testfabrics, Inc. in New Jersey.

All testing was carried out in a commercially available liquid laundry detergent, Cheer® "Free", purchased from a local super market. The liquid detergent was heat treated for 30 minutes at 95° C. to destroy cellulase activity (HT Cheer®) and E5 added at a concentration of 5 mg/L. Identical conditions were used in comparative testing with non-heat treated Cheer® and heat treated Cheer® without E5.

The treated swatches were compared to a set of standard rating swatches by a panel of testers who assigned a Surface Appearance Rating score. The standard rating swatches range from 0=(very fuzzy and pilled) to 7=(no fuzz or pills). The results were averaged and are shown in FIGS. 9 and 10.

Example 9
Stability of E5 in Liquid Detergent

E5 was tested for stability in liquid detergent. E5 or an isolated cellulase from *Trichoderma longibrachiatum* were incubated in Wisk® detergent at a temperature of 38° C. and a concentration of 1300 mg/l and 695 mg/l, respectively. Samples were extracted at various points in time and the remaining cellulase activity tested by the PAHBAH method as described in M. Lever, Anal. Biochem., vol. 47, pp. 273–279 (1972) (Assay conditions included: 12 mg/ml CMC substrate, 12 mM MOPS buffer, 30 min incubation at 40° C.).

The results are shown in FIG. 11. As shown in FIG. 11, the residual activity of E5 was essentially unchanged after incubation for 35 days whereas the residual activity of the cellulase derived from *T. longibrachiatum* dropped to nearly zero in less than 15 days.

Of course, it should be understood that a wide range of changes and modifications can be made to the preferred embodiment described above. It is therefore intended that the foregoing detailed description be understood in the context of the following claims, including all equivalents, which are intended to define the scope of this invention.

We claim:

1. A method of treating cellulosic material comprising contacting said material with a cellulase obtainable from *Thermomonospora fusca* corresponding to E5, a truncated E5, or a derivative thereof wherein said contacting takes place at a pH greater than 7.0 but less than about 10.0.

2. The method according to claim 1, wherein said truncated E5 is obtained through proteolytic cleavage.

3. The method according to claim 1, wherein said truncated E5 is obtained through genetic engineering techniques.

4. The method according to claim 1, wherein said cellulosic material comprises cellulose containing fabric.

5. The method according to claim 4, wherein said cellulose containing fabric is treated so as to effect a stonewashed effect.

6. The method according to claim 4, wherein said cellulose containing fabric is treated so as to improve the appearance and/or feel of said fabric.

7. The method according to claim 4, wherein said cellulase is incorporated into a detergent composition.

8. The method according to claim 6, wherein said cellulose containing fabric comprises a faded, colored fabric and said improvement comprises improving the appearance of said faded colored fabric by rejuvenating the color thereof.

9. The method according to claim 6, wherein the improvement comprises a softer or smoother feel to said fabric.

10. The method according to claim 1, wherein said cellulosic material comprises wood pulp.

11. The method according to claim 1, wherein said cellulosic material comprises animal feed or grain.

* * * * *